United States Patent
Langhans et al.

(10) Patent No.: US 11,764,821 B2
(45) Date of Patent: Sep. 19, 2023

(54) MOBILE PHONE CASE WITH EPINEPHRINE INJECTION PEN CARRYING FEATURE

(71) Applicant: Langhans Ventures LLC, St. Louis Park, MN (US)

(72) Inventors: Elizabeth Diane Langhans, Minneapolis, MN (US); Jessie Alexandra Benson, Minneapolis, MN (US)

(73) Assignee: LANGHANS VENTURES LLC, St Louis Park (MN)

( * ) Notice: Subject to any disclaimer, the term of this patent is extended or adjusted under 35 U.S.C. 154(b) by 529 days.

(21) Appl. No.: 16/250,318

(22) Filed: Jan. 17, 2019

(65) Prior Publication Data
US 2019/0260411 A1     Aug. 22, 2019

Related U.S. Application Data

(60) Provisional application No. 62/618,384, filed on Jan. 17, 2018.

(51) Int. Cl.
*H04B 1/3888*     (2015.01)
*H04M 1/02*     (2006.01)

(52) U.S. Cl.
CPC ........ *H04B 1/3888* (2013.01); *H04M 1/0208* (2013.01); *H04M 1/0249* (2013.01)

(58) Field of Classification Search
CPC .. H04B 1/3888; H04M 1/0208; H04M 1/0249
USPC .......................................................... 455/575
See application file for complete search history.

(56) References Cited

U.S. PATENT DOCUMENTS

| 3,949,743 A | * | 4/1976 | Shanbrom | A61H 33/12 |
| | | | | 128/200.14 |
| 2002/0020727 A1 | * | 2/2002 | Huggins, Jr. | A45C 11/24 |
| | | | | 224/240 |
| 2005/0183242 A1 | * | 8/2005 | Gartrell | A44C 5/0007 |
| | | | | 16/444 |

(Continued)

FOREIGN PATENT DOCUMENTS

| JP | 2012273660 A | * | 6/2014 | ........ A61J 7/00 |
| JP | 6029061 B2 | * | 11/2016 | ........ A61J 7/00 |

(Continued)

*Primary Examiner* — Charles N Appiah
*Assistant Examiner* — Nicole M Louis-Fils
(74) *Attorney, Agent, or Firm* — Viksnins Harris Padys Malen LLP

(57) ABSTRACT

A case assembly is provided having a mobile phone case and storage case that is designed to securely hold a mobile phone and an epinephrine injection pen concurrently. The case assembly includes the mobile phone case which is configured to securely contain a mobile phone therein. The mobile phone case includes a viewing region which allows an operator to view a screen of the mobile phone. The storage case is coupled to the mobile phone case and is configured to securely contain and allow access to an epinephrine injector pen. The mobile phone case is selectively moveable relative to the storage case between an open position and a closed position. The opening in the storage case is covered when the mobile phone case is in the closed position, and the opening in the storage case is open when the mobile phone case is in the open position.

13 Claims, 24 Drawing Sheets

(56) References Cited

U.S. PATENT DOCUMENTS

| | | | | |
|---|---|---|---|---|
| 2006/0247579 A1* | 11/2006 | Friedman | A61M 5/2033 | 604/197 |
| 2012/0287503 A1* | 11/2012 | Mase | G02B 30/35 | 359/462 |
| 2013/0157730 A1* | 6/2013 | McCormac | H04M 1/18 | 455/575.8 |
| 2013/0206614 A1* | 8/2013 | O'Neill | B23P 19/04 | 206/216 |
| 2014/0029197 A1* | 1/2014 | Hishinuma | G06F 1/1613 | 361/679.55 |
| 2014/0116895 A1* | 5/2014 | Ellenburg | H04B 1/3888 | 206/37 |
| 2014/0128132 A1* | 5/2014 | Cox, III | H04M 1/185 | 455/575.8 |
| 2014/0228082 A1* | 8/2014 | Morrow | H04B 1/3888 | 455/575.8 |
| 2015/0080806 A1* | 3/2015 | Pribitkin | A61M 5/2033 | 604/189 |
| 2015/0105903 A1* | 4/2015 | Denny | A61J 7/0076 | 700/237 |
| 2015/0189158 A1* | 7/2015 | Hailey | H04N 5/23293 | 348/333.12 |
| 2015/0328411 A1* | 11/2015 | Friedman | A61M 5/20 | 604/198 |
| 2016/0038689 A1* | 2/2016 | Lee | A61M 5/19 | 604/113 |
| 2017/0155419 A1* | 6/2017 | Greiner | H04B 1/3888 | |
| 2018/0099093 A1* | 4/2018 | Ebert | A61M 5/2033 | |
| 2018/0344004 A1* | 12/2018 | Kim | A45C 13/1069 | |
| 2019/0133280 A1* | 5/2019 | Gordon | G06J 1/1628 | |

FOREIGN PATENT DOCUMENTS

| | | | | |
|---|---|---|---|---|
| KR | 20150001868 U | * | 11/2013 | H04B 1/3888 |
| KR | 1491978 B1 | * | 2/2015 | A45C 11/00 |

* cited by examiner

MOBILE PHONE CASE WITH EPINEPHRINE INJECTION PEN CARRYING FEATURE

CROSS-REFERENCE TO RELATED APPLICATION(S)

This patent application claims the benefit of priority of U.S. application Ser. No. 62/618,384, filed Jan. 17, 2018, which application is herein incorporated by reference.

BACKGROUND OF THE INVENTION

The present invention relates to the field of mobile phone cases and in particular, mobile phone cases which are designed to facilitate utilization and transportation of the cell phone while at the same time providing a secure storage location.

While once considered a luxury item, mobile ("cell") phones have found widespread use throughout the world. One study found that in 2014, nearly 60 percent of the world population owned a mobile phone. Mobile phones are typically carried continuously by their owner and are often subject to harsh conditions including physical shocks. Mobile phone cases are known in the art and typically used to provide protection to a mobile phone. Some such cases may partially cover the mobile phone, while others may include a closeable cover.

Certain individuals are prone to severe allergic reactions. Some reactions are so severe that the patient can go into anaphylaxis. This is an extreme reaction, which can result in swelling of the airways, which can lead to unconsciousness or even death. Epinephrine injection pens can be carried by such individuals and used to administer an emergency dose of epinephrine during the onset of an allergic reaction to help prevent, or limit the severity, of anaphylaxis. Because the onset of anaphylaxis can be life threatening, susceptible individuals are advised to carry an epinephrine injection pen with them at all times. However, epinephrine pens can be difficult to keep track of, and although some pens are attachable to a belt, many users do not wear belts. For these and other reasons, there is a need for the subject matter of the present disclosure.

SUMMARY OF THE INVENTION

The present invention provides a case assembly having a mobile phone case and a storage case that is designed to securely hold both a mobile phone and an epinephrine injection pen concurrently.

The case assembly includes the mobile phone case which is configured to securely contain a mobile phone therein. The mobile phone case includes a viewing region which allows an operator to view a screen of the mobile phone. The storage case is coupled to the mobile phone case and is configured to securely contain an epinephrine injector pen. The storage case includes an opening formed therein allowing access to the epinephrine injector pen. The mobile phone case is selectively moveable relative to the storage case between an open position and a closed position. The opening in the storage case is covered when the mobile phone case is in the closed position, and the opening in the storage case is open when the mobile phone case is in the open position.

This device will lead to an increase in the number of persons who carry epinephrine injection pens, thereby leading to an increase in safety for themselves and for the persons around them.

BRIEF DESCRIPTION OF THE DRAWINGS

FIG. 8b is a top right side perspective view of the of the case assembly of FIG. 8a;

FIGS. 8c and 8d are respective bottom and top plan views of the case assembly of FIG. 8a;

FIGS. 8e and 8f are end views of the case assembly of FIG. 8a;

FIG. 9b is a top right side perspective view of the of the case assembly of FIG. 9a;

FIGS. 9d and 9e are respective top and bottom plan views of the case assembly of FIG. 9a;

FIGS. 10e and 10f are respective top and bottom plan views of the case assembly of FIG. 10a.

DETAILED DESCRIPTION OF THE INVENTION

Figure 1:
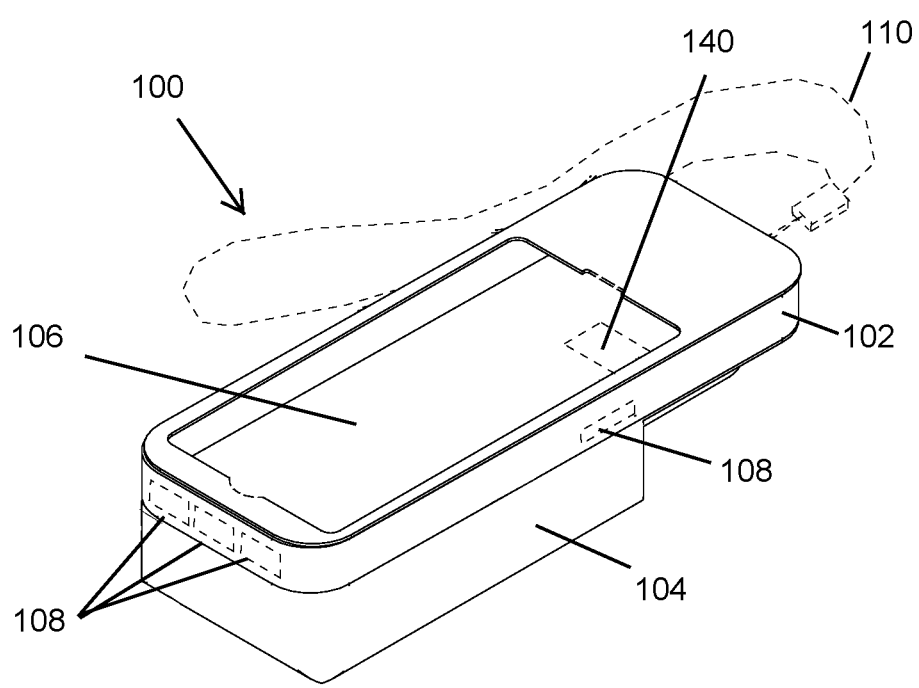
FIG. 1 is a top left side perspective view of a case assembly in accordance with one embodiment of the present invention in which a mobile phone case is in a closed position with respect to a storage case.

Certain versions of current mobile phone cases allow for the protection of the phone while also allowing for the concurrent transportation of items of importance to the user, such as credit cards, driver's license, and other useful items. However, there is an ongoing need for a mobile phone case that has been designed to safely carry an epinephrine injection pen, which to millions of people is an item of extreme importance. Many people who experience life threatening allergic reactions to outside stimuli do not carry an epinephrine injection pen on its own due to the inconvenience in carrying the item or out of forgetfulness. With this mobile phone case, users will be able to conveniently have an epinephrine injection pen on hand at all times by storing the pen in their case for their mobile phone that people carry with them at all times.

Exemplary manufacturing methods for forming the mobile phone case and the epinephrine injection pen holder include but are not limited to injection molding, structural foam molding, reaction injection molding, blow molding, and shaped thermoforming. In some embodiments, the case assembly is manufactured by a method including forming a mobile phone case, forming an epinephrine injection pen holder having an "L" shape, and coupling the mobile phone case to the epinephrine injection pen holder. In some embodiments, coupling the mobile phone case to the epinephrine injection pen holder includes providing one or more hinges to couple the mobile phone case to the epinephrine injection pen holder. Some embodiments further include coupling a mirror to the epinephrine injection pen holder. In some embodiments a mirror is mounted in the horizontal section of the pen storage case. In some embodiments, the method further includes coupling a lanyard to the mobile phone case. In some embodiments, the storage case is mounted to the rear of the phone case. In some embodiments, the storage case is mounted substantially diagonally across the phone case.

Referring now to the invention in more detail, in FIGS. 1-7 there is shown a case assembly 100 having an upper mobile phone case 102 and a lower storage case 104. The mobile phone case 102 includes an opening 106 formed therein whereby a screen of a mobile phone may be viewed and accessed by a user. The opening 106 may optionally be covered by a transparent window to protect the screen. Preferably, the transparent window is formed of a material that allows touch screen operation by the user. The mobile phone 102 case also includes access regions 108. Access regions 108 may be thinned regions or otherwise to allow the user to access buttons or other features of the mobile phone such as a charging port or a headphone jack. An optional hand strap or lanyard 110 is also illustrated.

Figure 2:
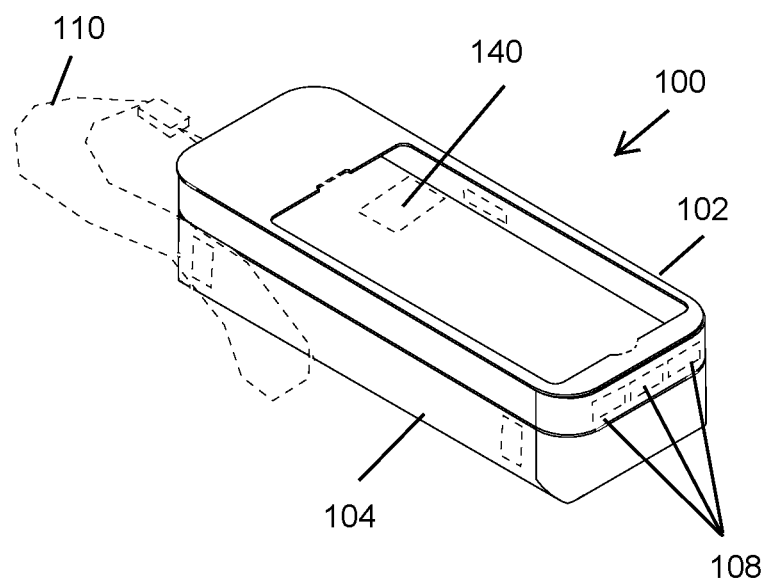
FIG. 2 is a top right side perspective view of the of the case assembly of FIG. 1.
Figure 3:
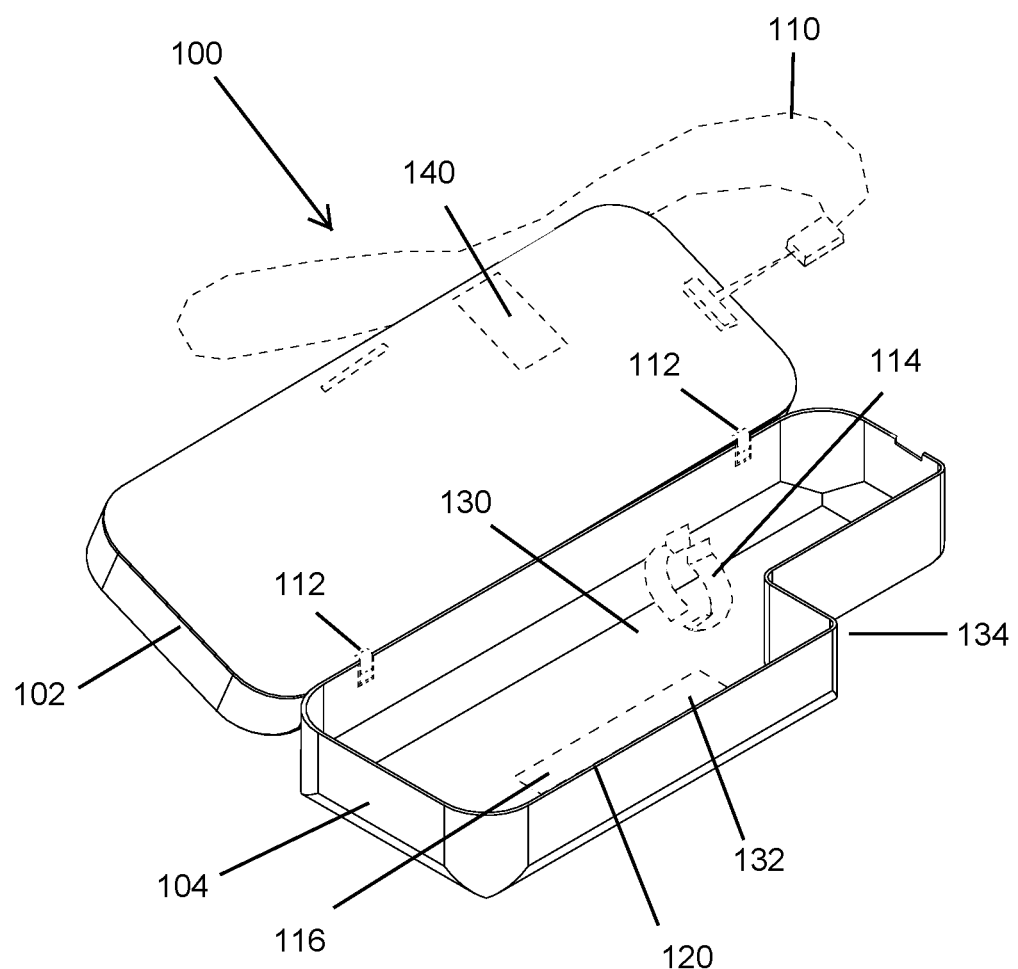
FIG. 3 is a top left side perspective view of the case assembly of FIG. 1 in which the mobile phone case is in an open position with respect to the storage case.
Figure 5:
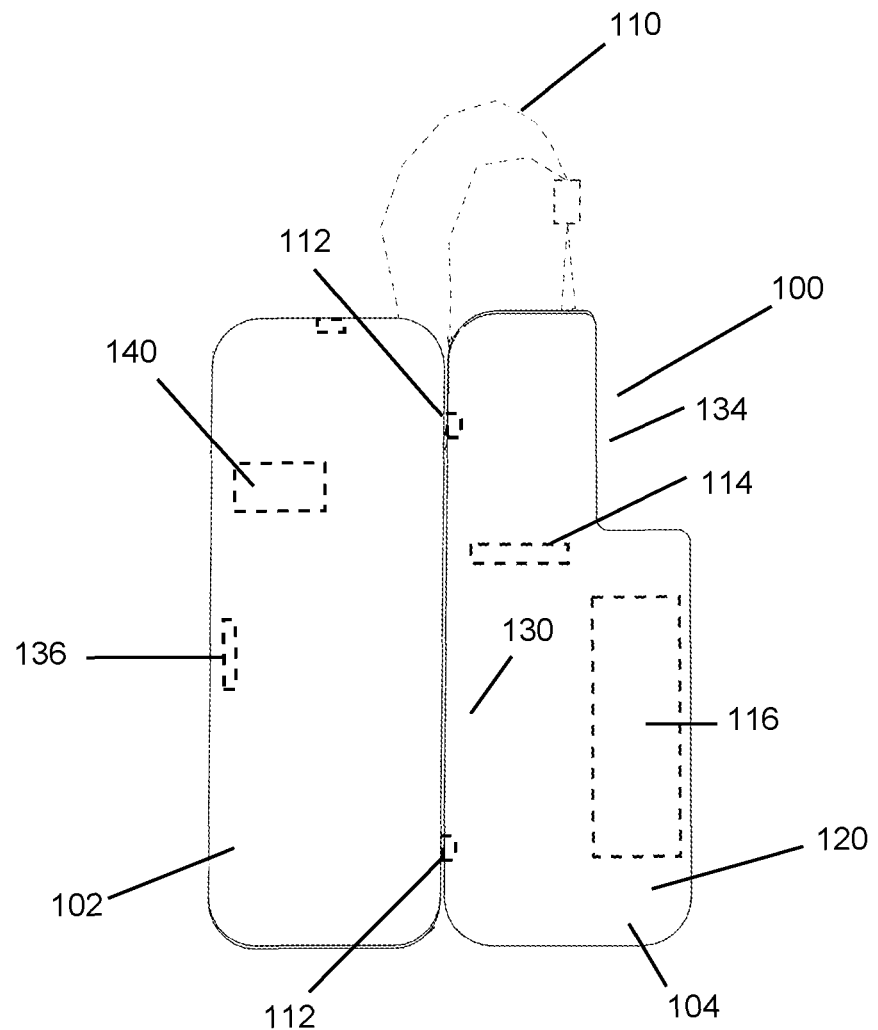
FIG. 5 is a bottom plan view of the case assembly of FIG. 1 with the mobile phone case in the open position.

In FIGS. 1 and 2, the mobile phone case 102 is in a closed position with respect to the storage case 104 whereby the storage case 104 is covered. However, in FIGS. 3 and 5, the mobile phone case 102 is shown in an open position in which an opening 120 of the storage case 104 is exposed. As illustrated in FIGS. 3 and 5, hinges 112 are used to secure the mobile phone case 102 to the storage case 104. The hinges 112 allow the mobile phone case to be selectively moved between an open position as illustrated in FIG. 3 and the closed position illustrated in FIGS. 1 and 2. The storage case 104 includes an epinephrine injector pen holder 114. The holder 114 is formed as a plastic snap clamp into which a pen can be placed in securely held in position. FIGS. 3 and 5 also show an optional mirror 116. The mirror 116 is not limited to a particular type of mirror. Exemplary mirrors suitable for use in connection with the cell phone case of the present disclosure include plane mirrors, convex mirrors, and concave mirrors. In some embodiments, the mirror 116 includes and is mounted on a rotatable mount to provide improved viewing of a epinephrine injection pen injection site.

The storage case 104 is formed in a "L" shape. "L" shape means having a shape substantially in the form of the letter "L". The "L" includes a vertical region or section 130 and a horizontal region or section 132. This leaves a cutout or open region 134. As also illustrated in FIGS. 3 and 5, mobile phone case 102 includes a window or opening 140. In the closed position, opening 140 is aligned with cutout region 134. This allows a camera of a mobile phone to be used when the case assembly 100 is in a closed position.

Figure 4A:
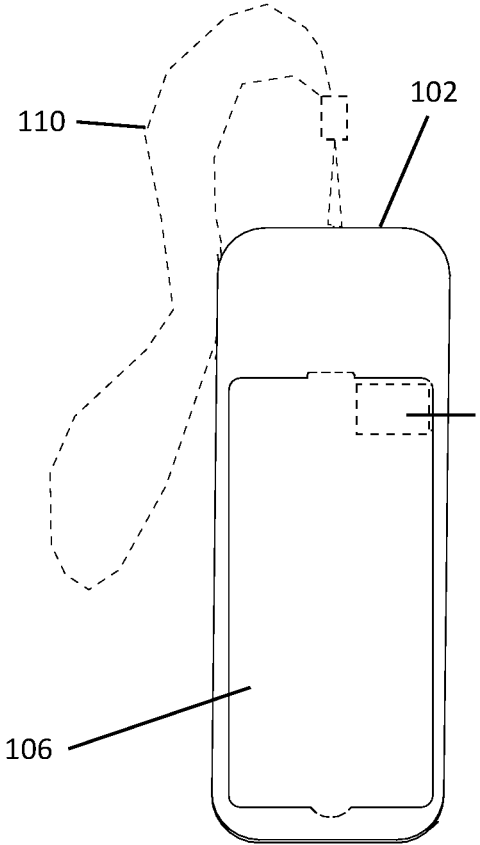
FIGS. 4a and 4b are respective top and bottom plan views of the case assembly of FIG. 1.
Figure 4B:
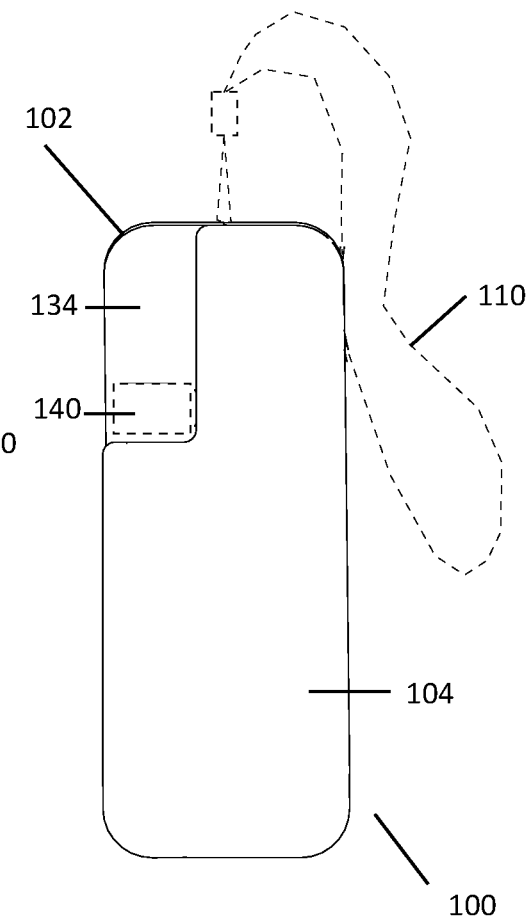

FIG. 4a is a top plan view and FIG. 4b is a bottom plan view of the case assembly 100. In FIGS. 4a and 4b the case assembly 100 is shown in a closed position.

FIG. 5 shows a latch 136 that can be used to secure the case assembly 100 in a closed position. Latch 136 can be any type of latching mechanism including but not limited to a mechanical clasp, a magnet based latch, a hook and loop fasteners.

Figure 6:
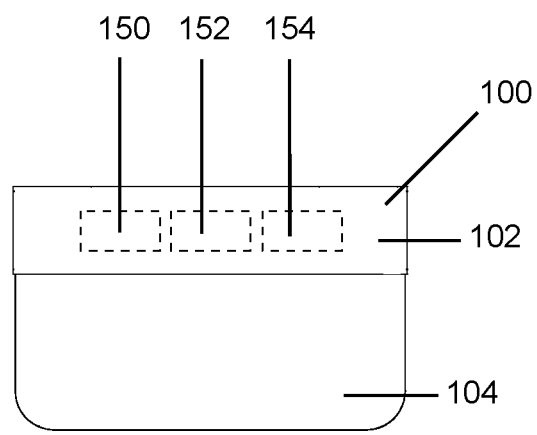
FIGS. 6 and 7 are end views of the case assembly of FIG. 1.
Figure 7:
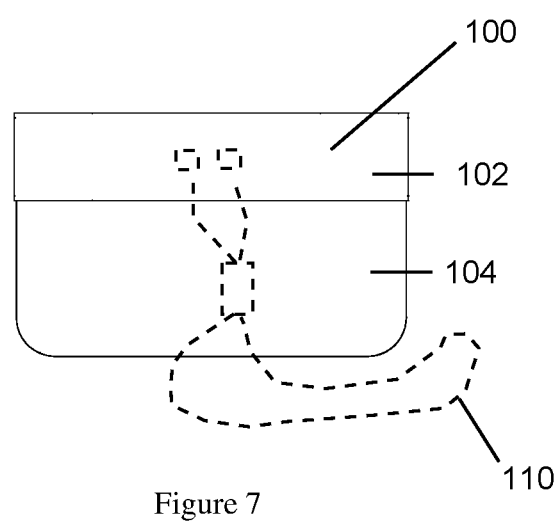

FIG. 6 is a top end view of the case assembly 100 showing three openings in the case body as 150, 152, and 154. These may be used to access to allow access to the mobile phone speakers, headphone and power jacks while allowing the case to remain on. FIG. 7 is a bottom end view showing optional lanyard 110 attached to the mobile phone case 102.

FIGS. 8a-8f show an alternative configuration of the case assembly 200 having a mobile phone case 202 and an attached rear storage case 204 for housing an epinephrine injection pen.

Figure 8A:
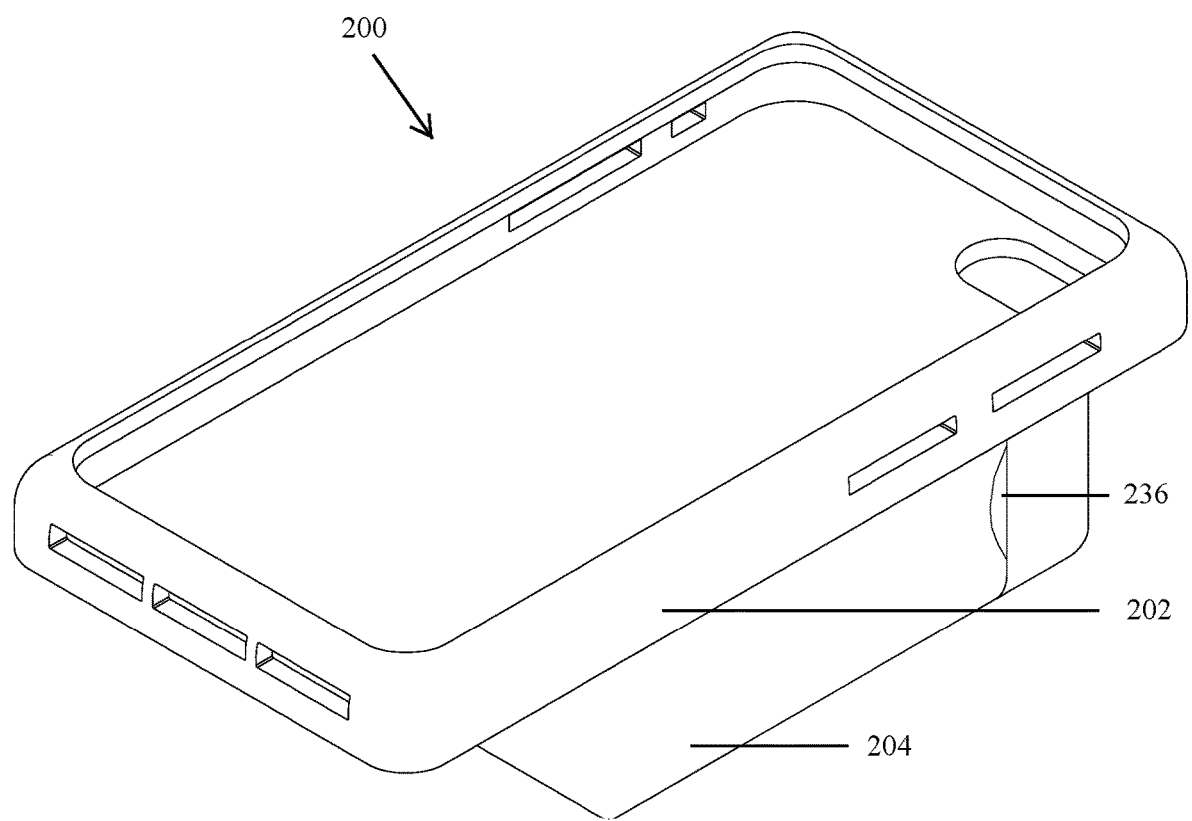
FIG. 8a is a top left side perspective view of a case assembly in accordance with one additional embodiment of the present invention in which a mobile phone case is attached to a rear cubic storage unit, which is in a closed position.
Figure 8B:
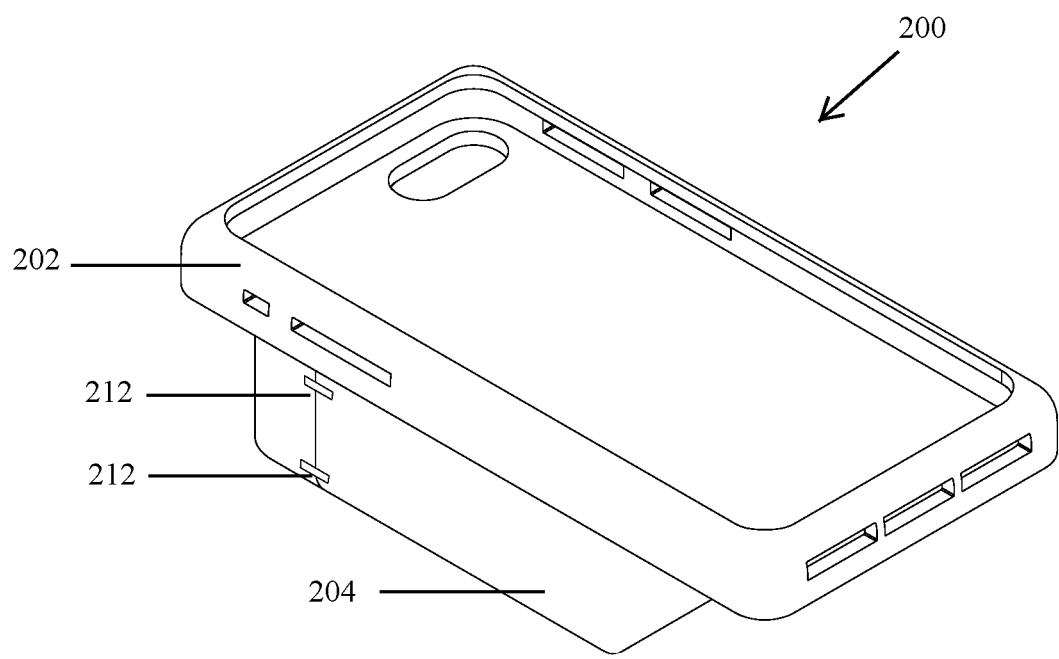

In FIGS. 8a and 8b, the case assembly 200 is a mobile phone case 202 is attached to an external cubic storage case 204 whereby the storage case 204 is in a closed position. The external storage case 204 itself is an epinephrine injector pen holder. "Cubic storage" means having a shape substantially in the form of being able to house a cube shaped object.

FIG. 8a shows a latch 236 that can be used to secure the case assembly 200 in a closed position. Latch 236 can be any type of latching mechanism including but not limited to a mechanical clasp, a magnet-based latch, a hook and loop fasteners.

FIG. 8b shows hinges 212 that are used to secure the mobile phone case 202 to the storage case 204. The hinges 212 allow the storage case 204 to be selectively moved between an open and closed position. The interior of storage case 204 is an epinephrine injector pen holder.

Figure 8C:
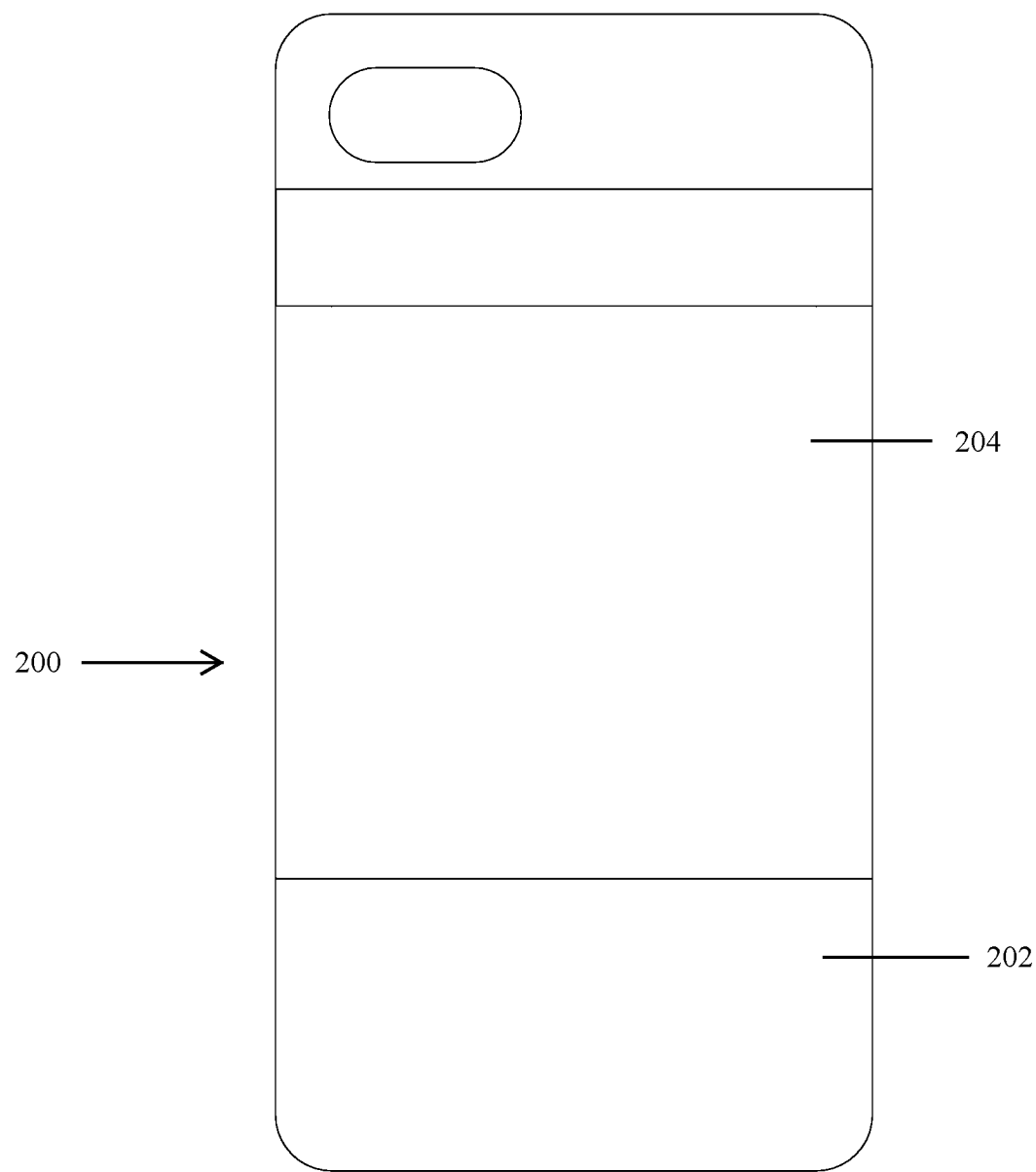
Figure 8D:
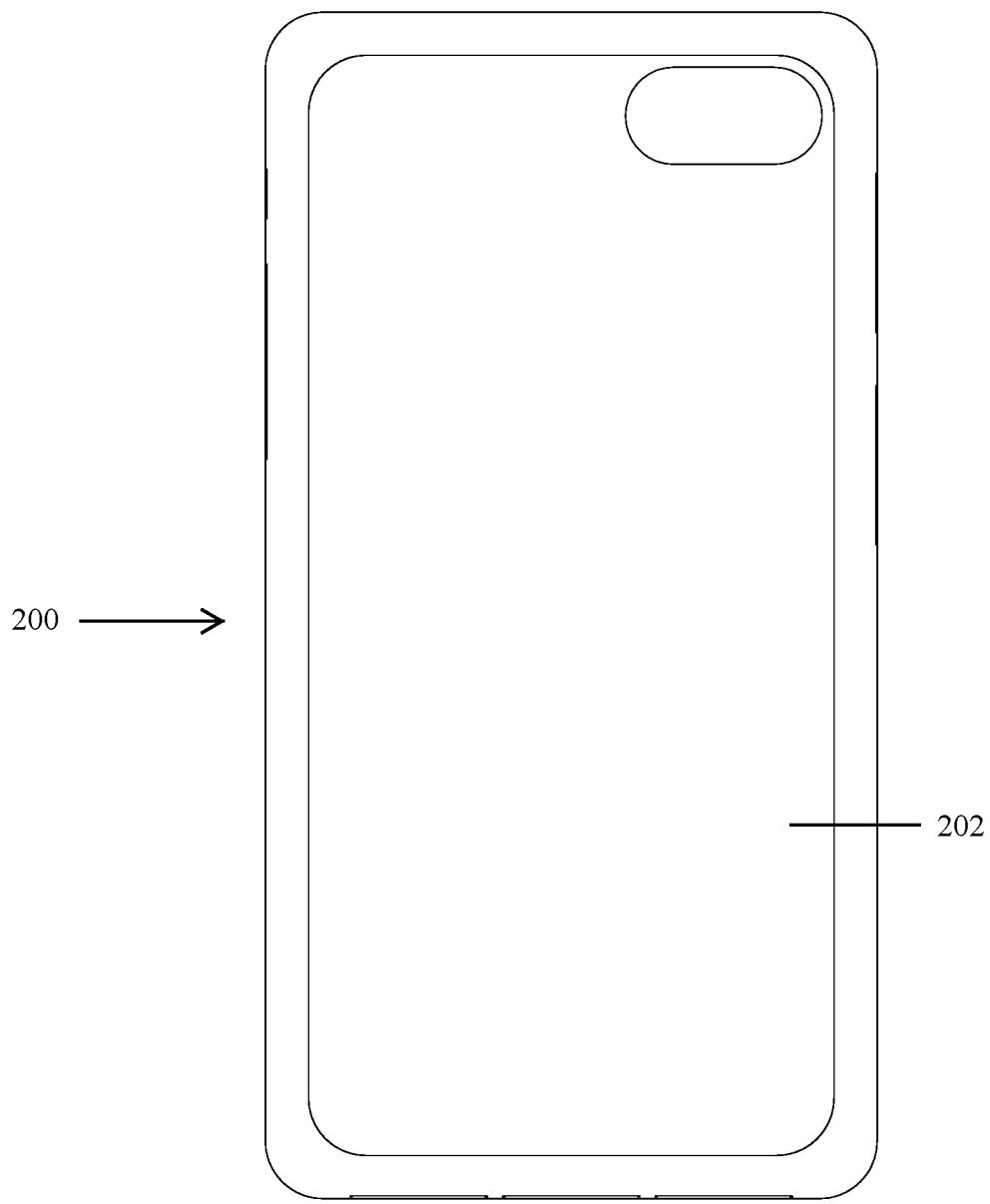

FIG. 8c is a bottom plan view of the case assembly 200 and FIG. 8d is a top plan view of the case assembly 200. In FIGS. 8c and 8d the case assembly 200 is shown in a closed position.

Figure 8E:
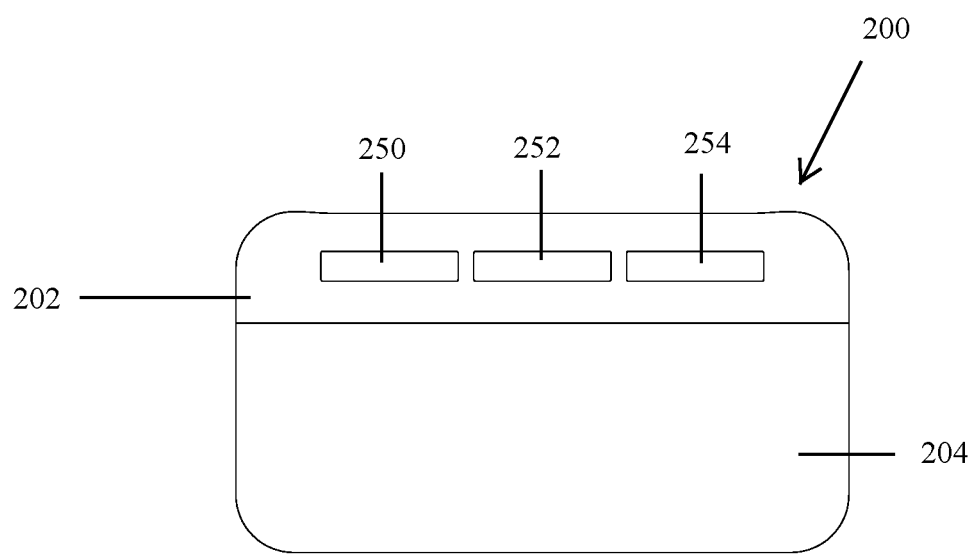
Figure 8F:
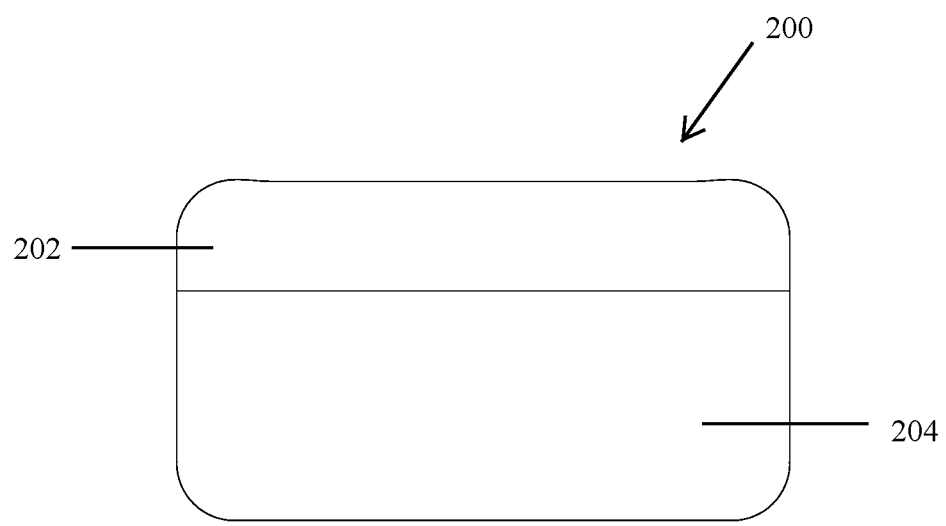

FIG. 8e is a bottom end view of the mobile phone case 202 of the case assembly 200 showing three openings in the case body as 250, 252, and 254. These may be used to access to allow access to the mobile phone speakers, headphone and power jacks while allowing the case to remain on. FIG. 8f is a top end view of the mobile phone case 202 of the case assembly 200.

FIGS. 9a-9e show an alternative configuration of case assembly 300 of the mobile phone case 302 is attached to an external semi-cylindrical storage case 304. The external semi-cylindrical storage case 304 itself is an epinephrine injector pen holder. An advantage of a semi-cylindrical shaped pen case is that it reduces the amount of material used in the case, decreases the cost, and provides for easy and quick of extraction of the pen from the case.

Figure 9A:
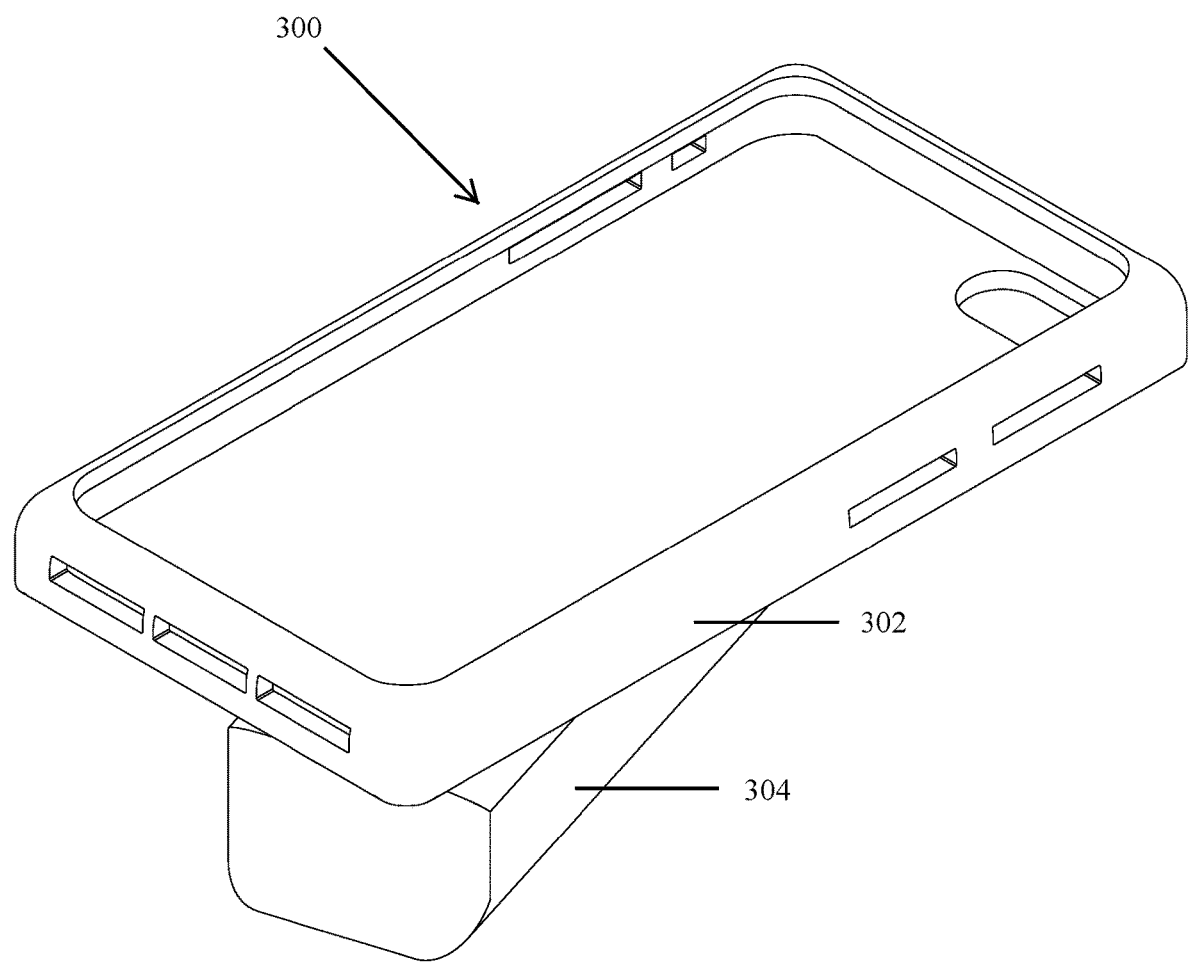
FIG. 9a is a top left side perspective view of a case assembly in accordance with one additional embodiment of the present invention in which a mobile phone case is attached to a rear cylindrical storage unit, which is in a closed position.
Figure 9B:
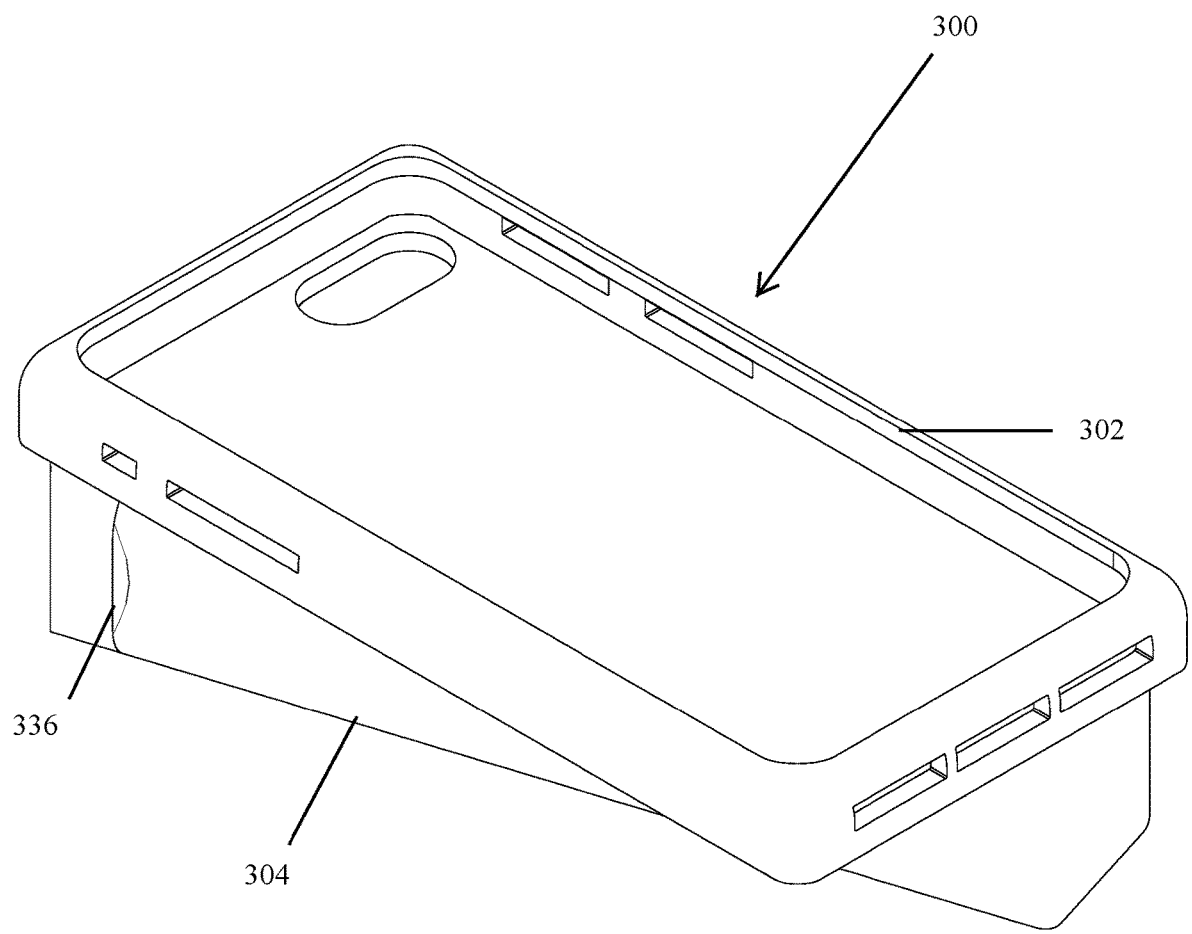

FIG. 9b shows a latch 336 that can be used to secure the external semi-cylindrical storage case 304 in a closed position in case assembly 300. Latch 336 can be any type of latching mechanism including but not limited to a mechanical clasp, a magnet-based latch, a hook and loop fasteners.

Figure 9C:
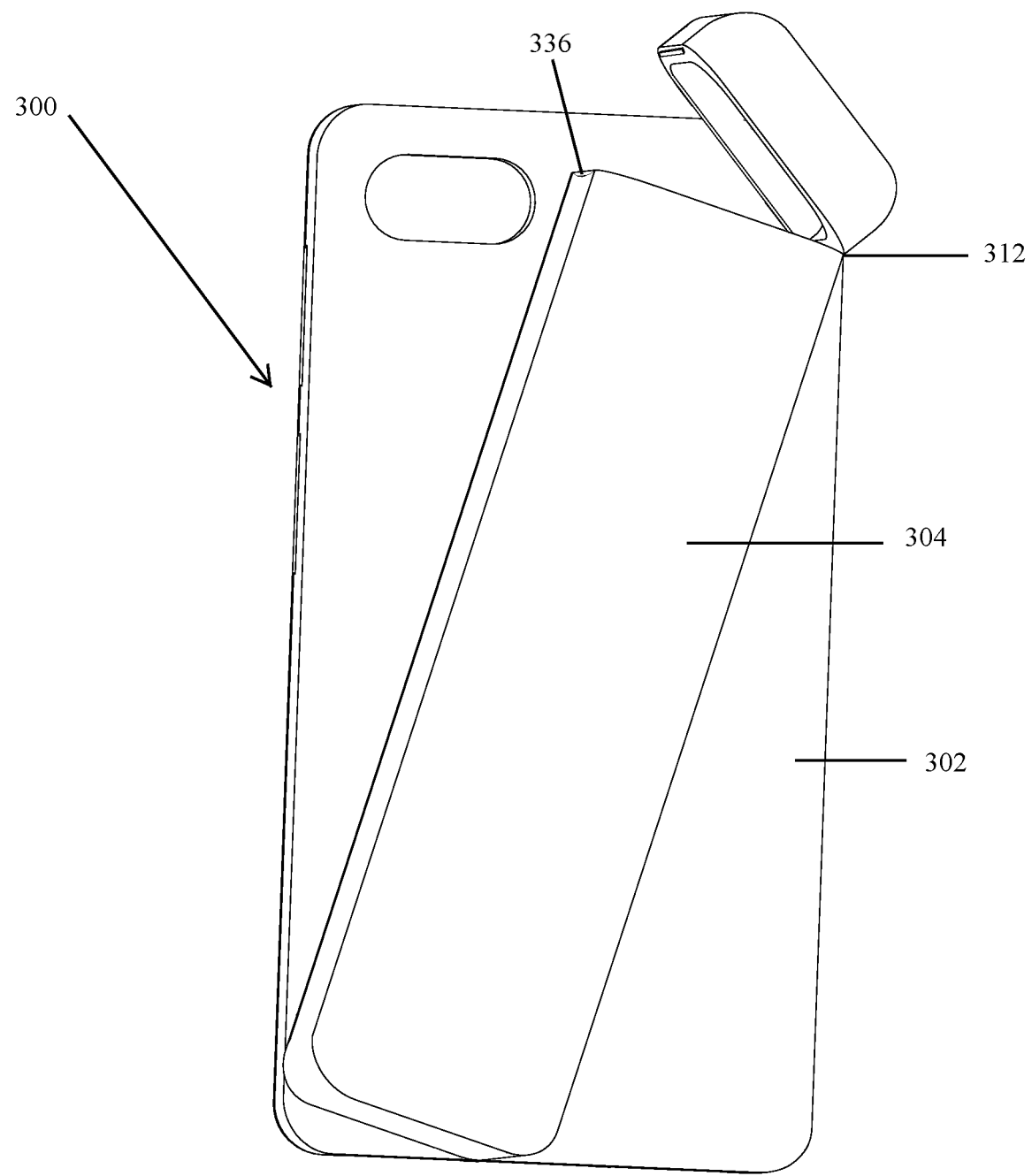
FIG. 9c is a bottom plan view of the case assembly of FIG. 9a in which the mobile phone case is attached to a rear cylindrical storage case, which is in an open position.

FIG. 9c shows hinges 312 that allow the external semi-cylindrical storage case 304 to be selectively moved between an open and closed position. The external semi-cylindrical storage case 304 is shown in an open position. The interior of external semi-cylindrical storage case 304 is an epinephrine injector pen holder.

Figure 9D:
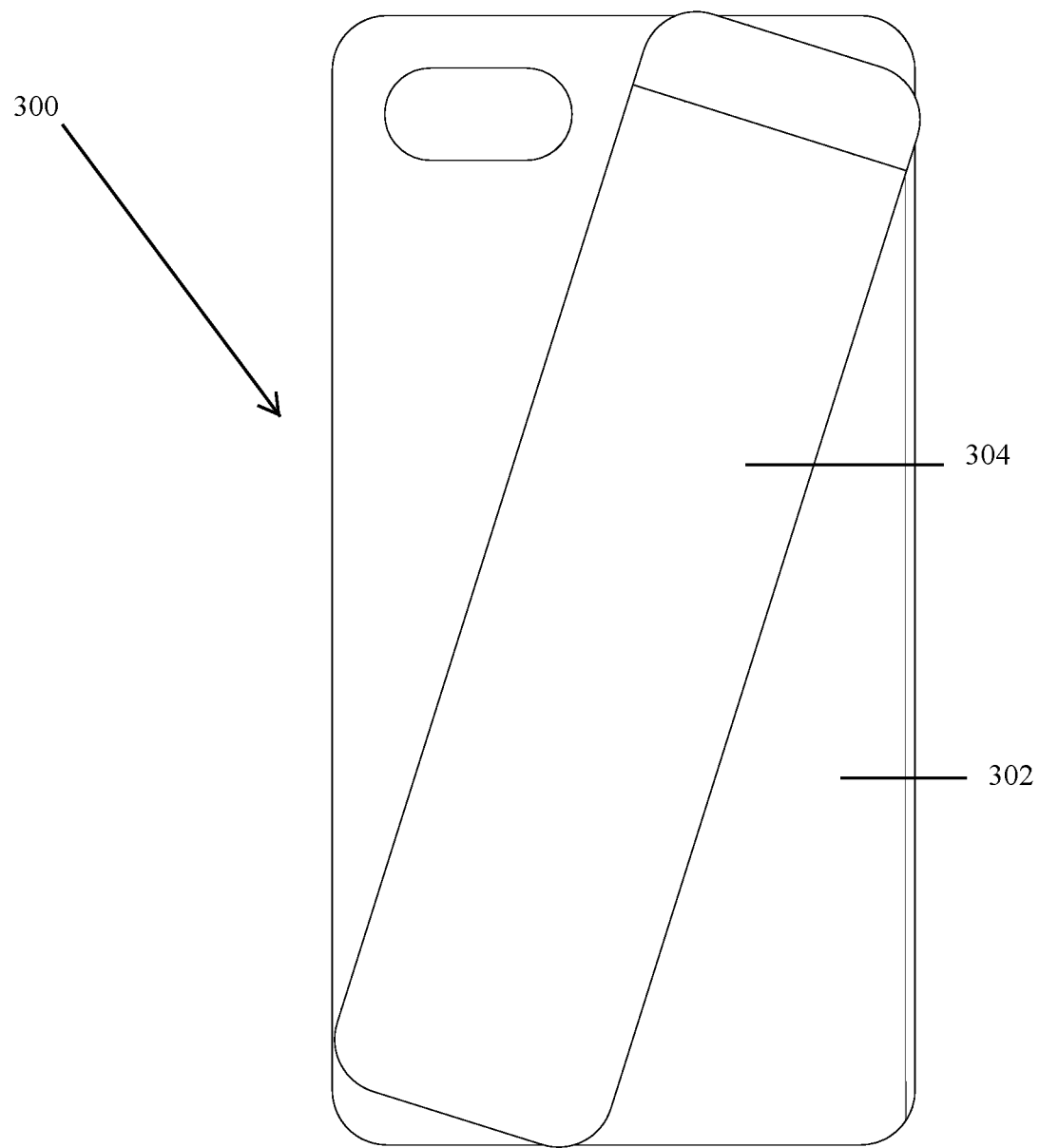
Figure 9E:
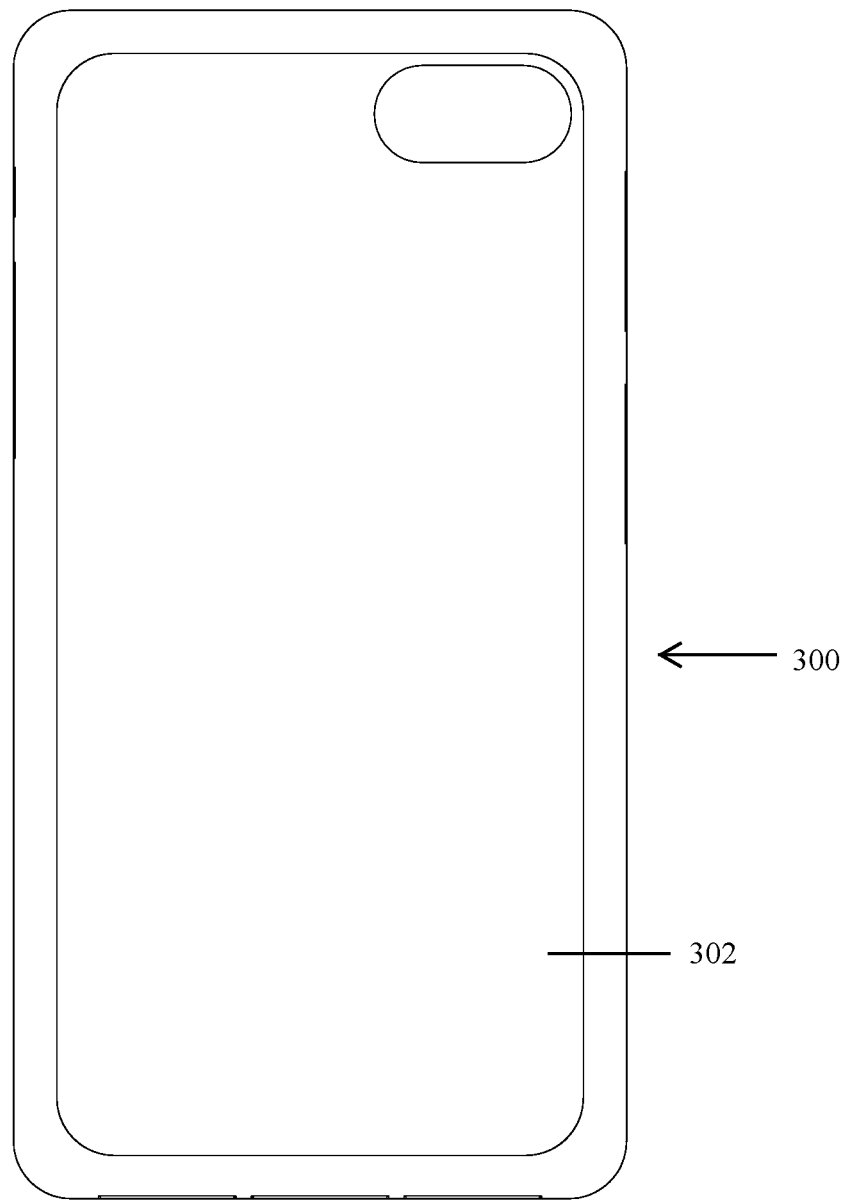

FIG. 9d is a bottom plan view of the case assembly 300 showing the external semi-cylindrical storage case 304 in a closed position and FIG. 9e is a top plan view of the mobile phone case 302 of the case assembly 300.

FIGS. 10a-10f show an alternative configuration of case assembly 400 of the mobile phone case 402 is attached to an external semi-cylindrical storage case 404. The external semi-cylindrical storage case 404 itself is an epinephrine injector pen holder/housing. Additionally, attached loops 424 of the same material as the mobile phone case 402 are placed for the user's fingers to rest while holding the case in hand.

Figure 10A:
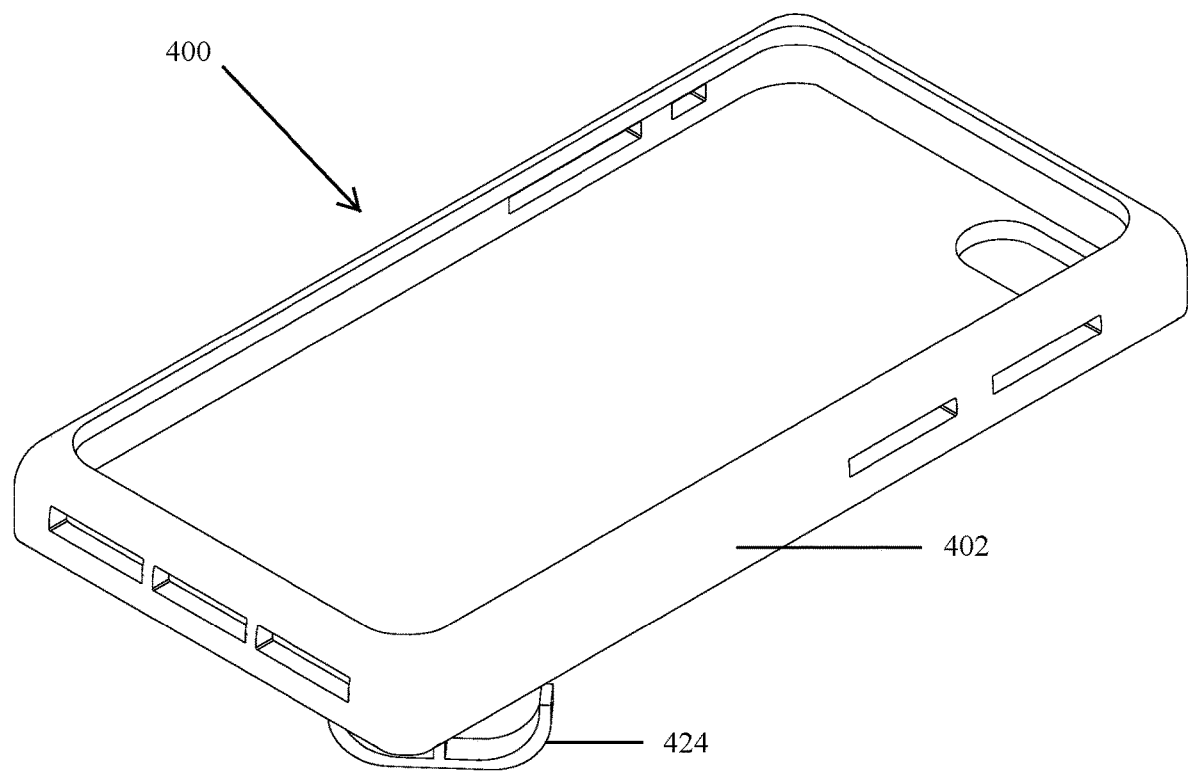
FIG. 10a is a top left side perspective view of a case assembly in accordance with one additional embodiment of the present invention in which the mobile phone case is attached to a rear cylindrical storage unit, which is in a closed position, and attached loops for the user's fingers with respect to the storage unit.

FIG. 10a shows the placement of the loops 424 in relation to the mobile phone case 402 in the case assembly 400.

Figure 10B:
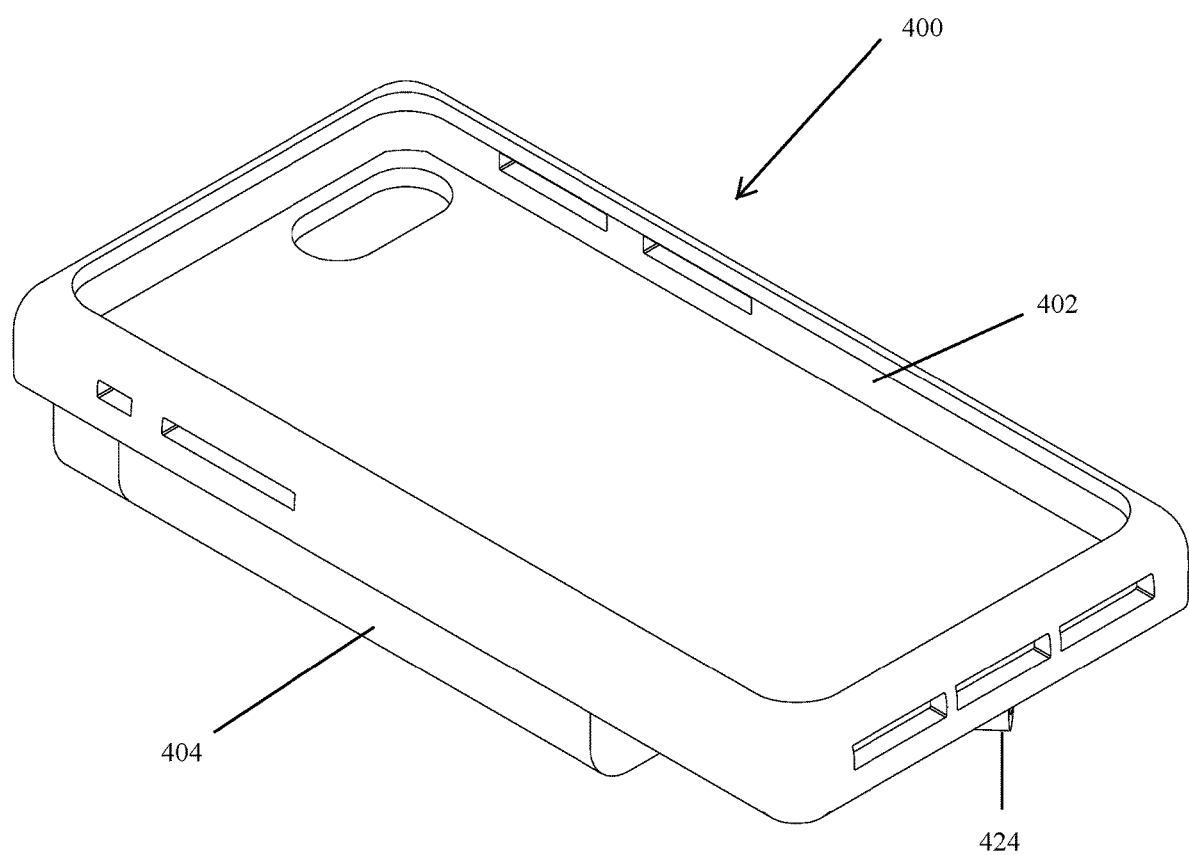
FIG. 10b is a top right side perspective view of the case assembly of FIG. 10a in which the mobile phone case has an attached cylindrical storage unit which is in a closed position and attached loops for the user's fingers with respect to the storage unit.

FIG. 10b shows the placement of the external semi-cylindrical storage case 404, which is in a closed position, in relation to the loops 424 on the mobile phone case 402 in the case assembly 400.

Figure 10C:
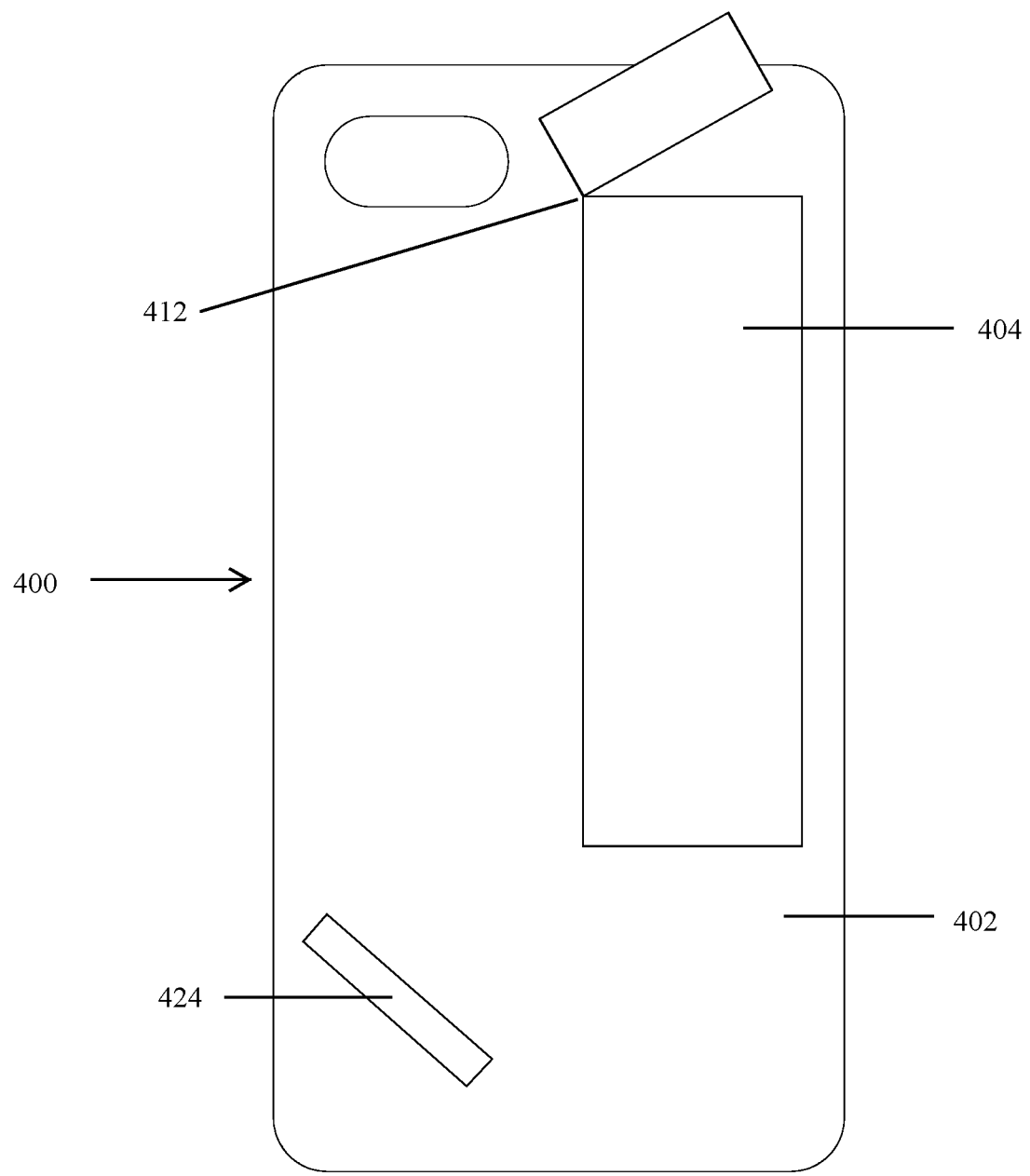
FIG. 10c is a back perspective view of the case assembly of FIG. 10a in which the mobile phone case has an attached storage unit which is in an open position and attached loops for the user's fingers with respect to the storage unit.
Figure 10D:
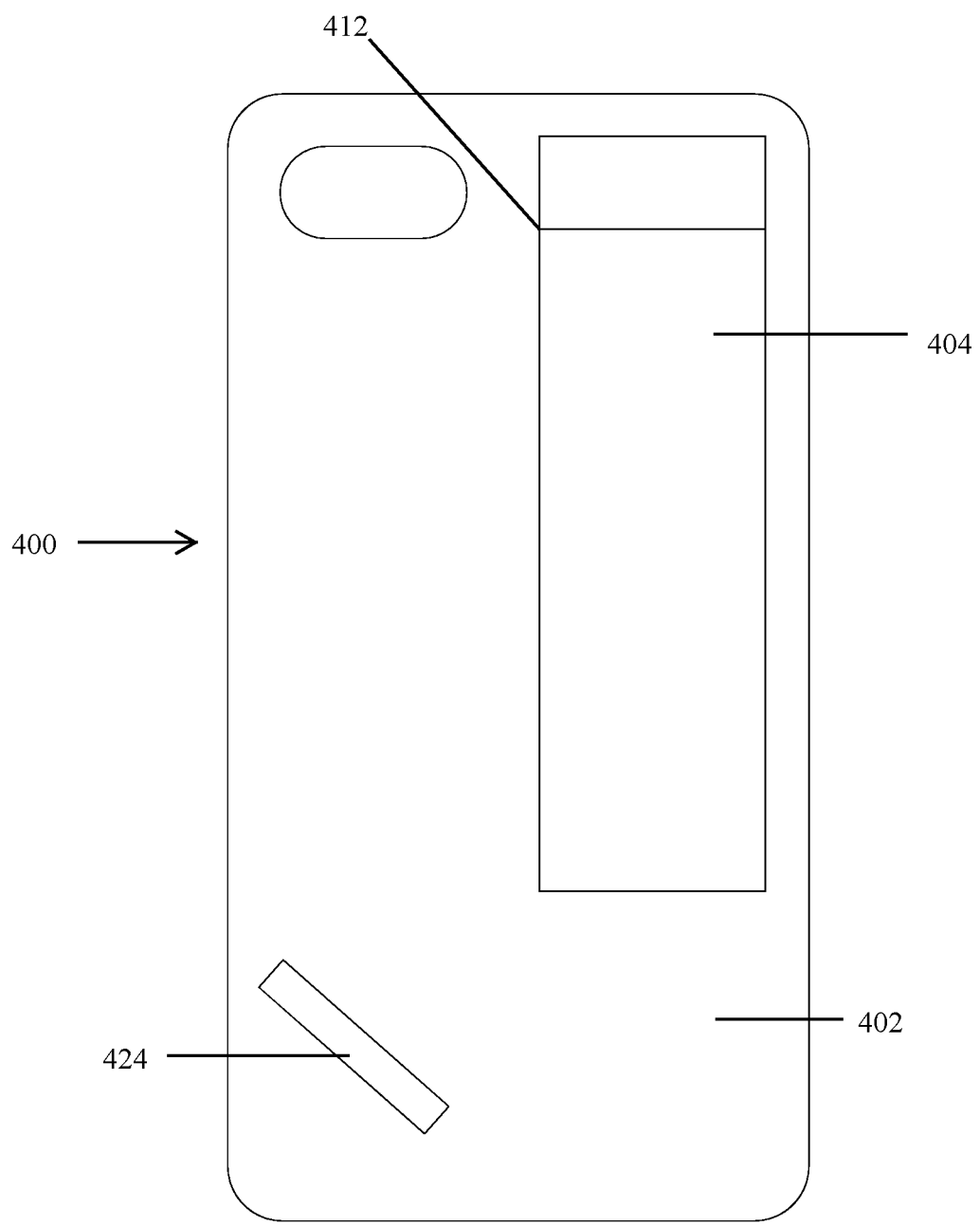
FIG. 10d is a back perspective view of the case assembly of FIG. 10a in which the mobile phone case has an attached storage unit which is in a closed position and attached loops for the user's fingers with respect to the storage unit.

FIGS. 10c and 10d are bottom plan views of the case assembly 400 showing the hinges 412 which allow the external semi-cylindrical storage case 404 to be move between an open and closed position.

Figure 10E:
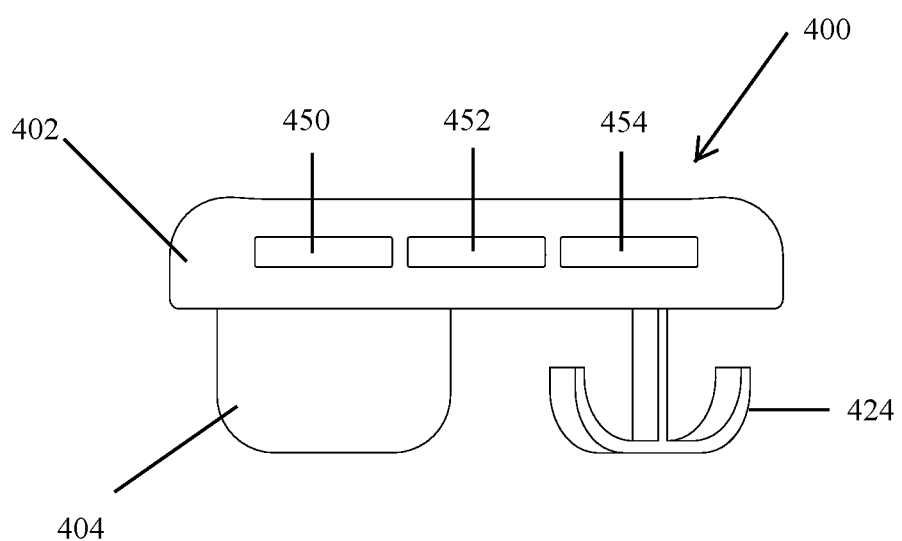
Figure 10F:
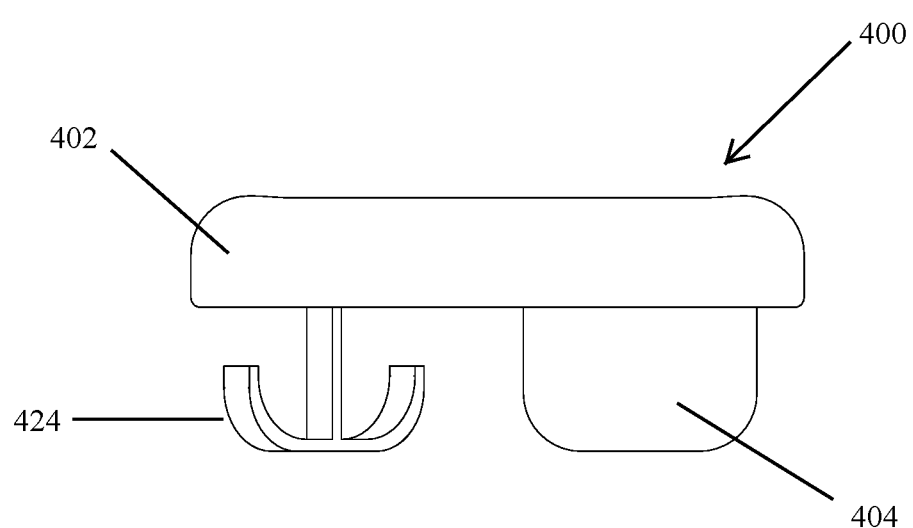

FIG. 10e is a bottom end view of the mobile phone case 402 of the case assembly 400 showing three openings in the case body as 450, 452, and 454. These may be used to access to allow access to the mobile phone speakers, headphone and power jacks while allowing the case to remain on. FIG. 10f is a top end view of the mobile phone case 402 of the case assembly 400.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. The hinges illustrated herein may be fabricated of any appropriate material. In one configuration, metal or plastic hinges are used. In another configuration, a hinge is formed using a bendable material such as a rubber, plastic, and fabric. The hinges hold together the front phone housing area to the back storage compartment such that one can swing relative to the other, having two interlocking plastic leaves creating a locking clamp closure about which the two plastic leaves pivot. A hinged clasp is a device with interlocking parts for use in securing holding an epinephrine injection pen and a hinge for enabling easier insertion of the pen into the clasp. Although an "L" shape is illustrated, the storage case may be arranged in any configuration. Other opening configurations may also be provided for a camera of the cell phone or for access to other components of the cell phone. A securing mechanism or clamp may also be provided. For example, a front snap clasp mechanism can be used to hold the front phone housing area to the back storage compartment in a closed position, which protects the inner storage area and epinephrine injection pen from disturbance when not needed. Although a clamp is illustrated, any attachment mechanism may be used to secure an epinephrine injector pen in the storage case 104. For example, a flexible plastic snap clamp can be used and built into the back storage compartment, which allows the epinephrine injection pen to securely snap into the structure of the case for safe storage when not in use.

The various case openings for venting, front screen, and camera visibility may optionally have curved edges instead of sharp lines for comfort, visibility and durability. In one configuration, a soft texture is added to a plastic case exterior to provide a non-slip surface with a soft satin like feel.

The design of the pen case of the present disclosure has the advantage of being flexible enough to provide for carrying pens having a variety of shapes and sizes. For example, the hinged clasp is capable of securing both "thin" and "thick" pens.

The invention claimed is:

1. A case assembly, comprising:
a mobile phone case configured to securely contain a mobile phone therein, the mobile phone case including a viewing region which allows an operator to view a screen of the mobile phone; and
a storage case coupled to the mobile phone case and configured to securely contain an epinephrine injector pen, wherein the storage case includes an opening formed therein allowing access to the epinephrine injector pen;
wherein the mobile phone case is selectively moveable relative to the storage case between an open position and a closed position and the opening in the storage case is covered when the mobile phone case is in the closed position, and the opening in the storage case is open when the mobile phone case is in the open position.

2. The case assembly of claim 1, wherein the storage case includes an epinephrine injector pen clamp configured to clamp onto the epinephrine injector pen.

3. The case assembly of claim 1, wherein the mobile phone case is coupled to the storage case by a hinge.

4. The case assembly of claim 1, wherein the storage case has an "L" shape configured to contain the epinephrine injector pen in a vertical section of the "L" shape.

5. The case assembly of claim 4, wherein a horizontal section of the "L" shape is configured to provide additional storage.

6. The case assembly of claim 4, wherein a horizontal section of the "L" shape is configured to carry a mirror.

7. The case assembly of claim 4, wherein a cutout section of the "L" shape is configured to provide an opening for a camera of the mobile phone.

8. The case assembly of claim 1, wherein the storage case has a camera opening formed therein to provide access to a camera of the mobile phone.

9. The case assembly of claim 8, wherein the mobile phone case has an opening formed therein which aligns with the camera opening of the storage case when the mobile phone case is in the closed position.

10. The case assembly of claim 1, including a hinged clasp configured to secure the mobile phone case to the storage case.

11. The case assembly of claim 1, including a transparent material which covers the viewing region.

12. The case assembly of claim 3, wherein the hinge comprises a mechanical hinge.

13. The case assembly of claim 3, wherein the hinge comprises a bendable material.

\* \* \* \* \*